US007320447B1

(12) United States Patent
Lynch

(10) Patent No.: US 7,320,447 B1
(45) Date of Patent: Jan. 22, 2008

(54) BREATHER HOSE SUPPORTING APPARATUS

(76) Inventor: Spencer Lynch, 16 Bryn Mawr Dr., Rehoboth Beach, DE (US) 19971

( * ) Notice: Subject to any disclaimer, the term of this patent is extended or adjusted under 35 U.S.C. 154(b) by 328 days.

(21) Appl. No.: 11/215,175

(22) Filed: Aug. 31, 2005

(51) Int. Cl.
*F16L 3/16* (2006.01)
(52) U.S. Cl. .................. 248/49; 248/65; 128/200.24
(58) Field of Classification Search .............. 248/49, 248/65, 200, 205.1, 220.21, 309.1; 128/200.24
See application file for complete search history.

(56) References Cited

U.S. PATENT DOCUMENTS 4,349,015 A * 9/1982 Alferness ................. 601/41
5,814,213 A * 9/1998 Glasgow .................. 210/104
5,823,185 A * 10/1998 Chang .................. 128/204.18

* cited by examiner

*Primary Examiner*—Amy J. Sterling

(57) ABSTRACT

A hose guide includes a base plate that has top and bottom surfaces. The top surface includes a fastening member. The bottom surface includes guides extending downward therefrom. One guide has an eyelet adjacent to a base plate end portion. The bottom surface has a protrusion extending downwardly therefrom that has an aperture with a lip extending inwardly thereabout. An annular hose support has an aperture for receiving hoses therethrough, a concave outer surface, and fingers for connecting to the protrusion. The fingers engage the lip. The hose support further includes a permanently connected inner layer. The hose guide includes a tether and an annular stop member. The stop member has flanges. One flange has an aperture that receives the tether therethrough. The stop member is spaced from the attaching mechanism. A mechanism is included for attaching the hose guide to a support surface.

18 Claims, 5 Drawing Sheets

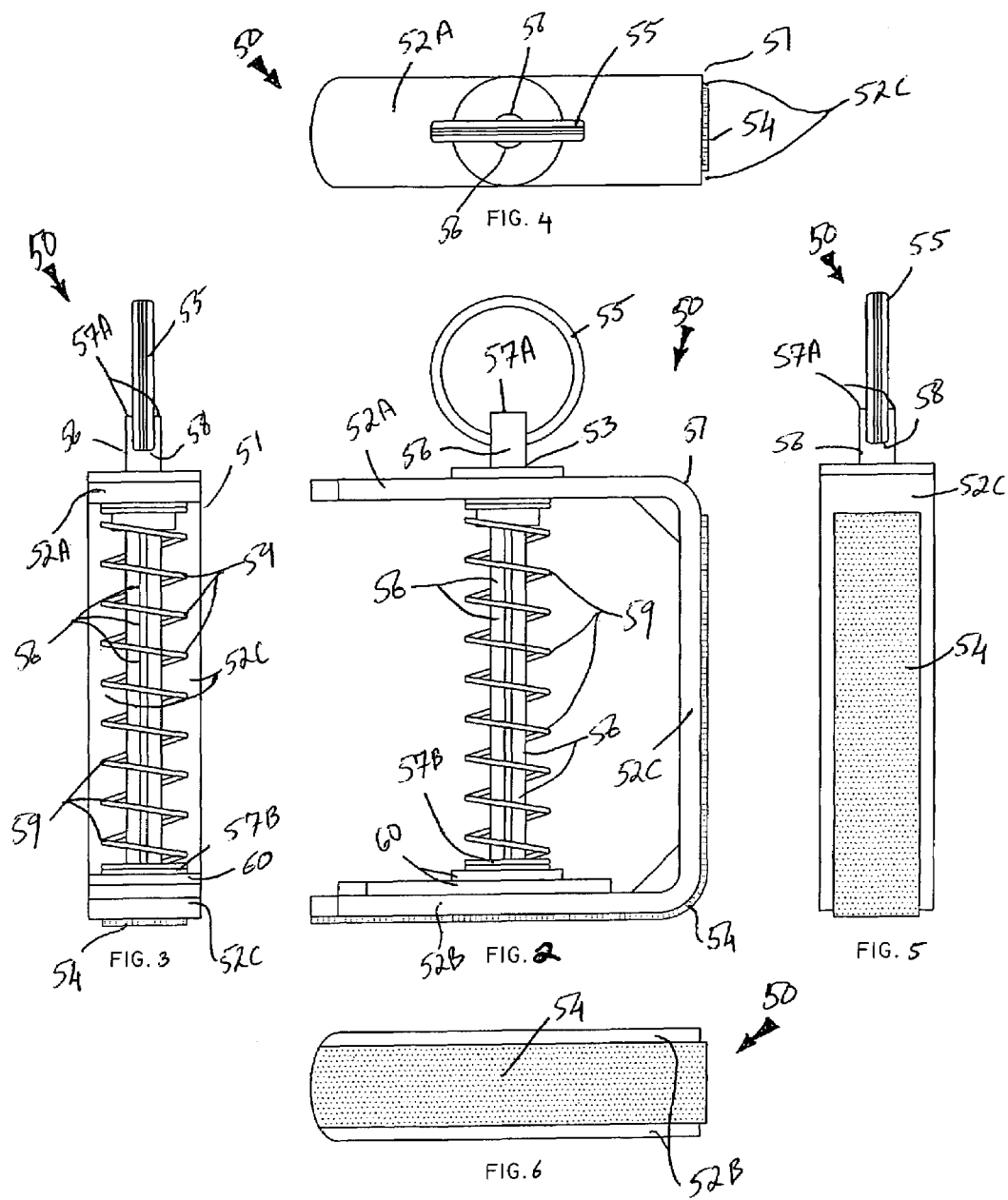

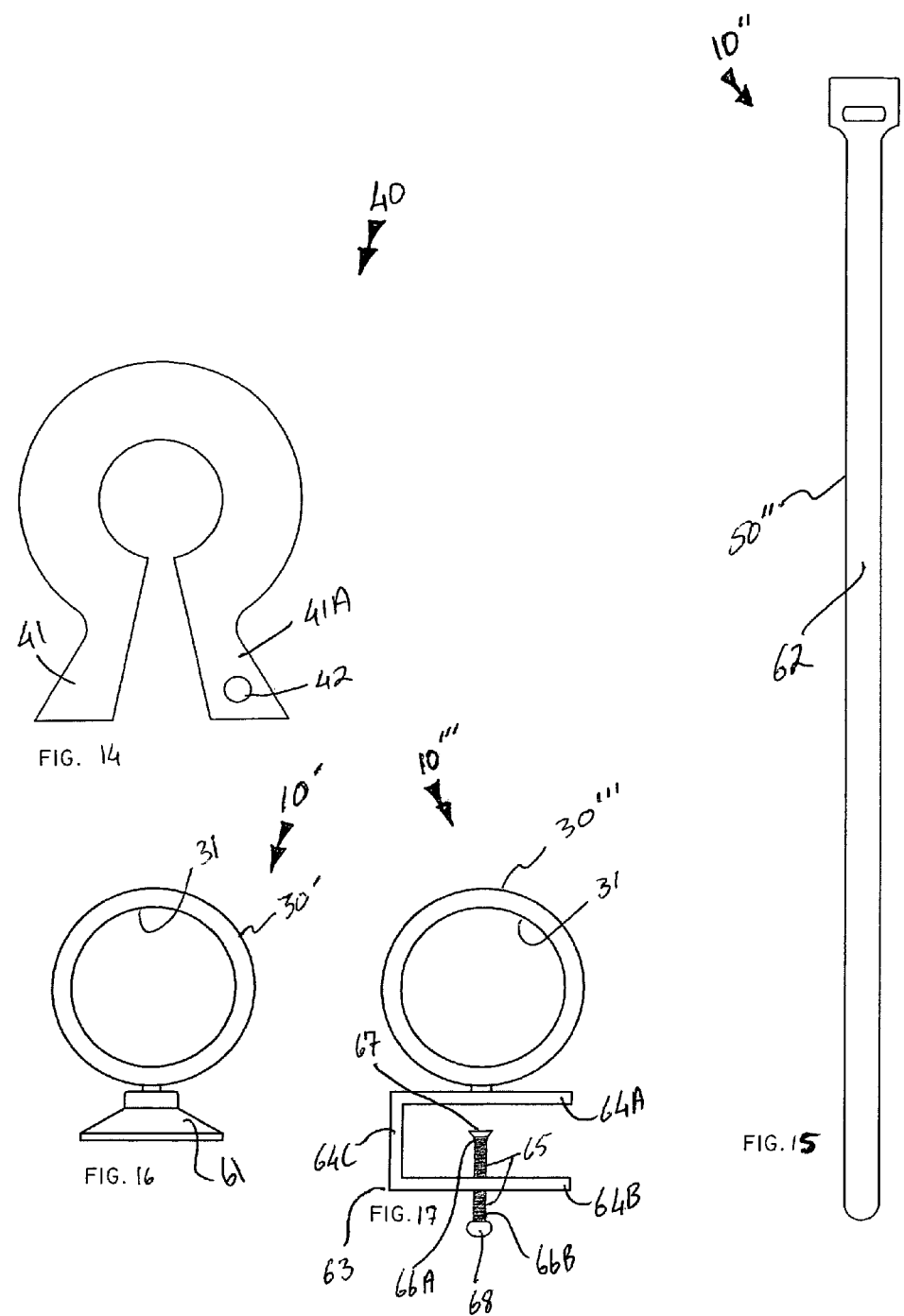

BREATHER HOSE SUPPORTING APPARATUS

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to hose guides and, more particularly, to a directional hose guide for supporting breather hoses in a medical care environment.

2. Prior Art

With the advent of technology, the medical field has seen an increase in the use of electronic equipment to assist individuals with their breathing and to assist medical personnel in monitoring their patients. As the design of such equipment would have it, there is a need for the patient to be connected to the device to allow proper functioning thereof. For example, respirators are coupled to the patient via a number of tubes that deliver oxygen to them and heart rate monitors are connected to the patient through a number of electrodes directly attached to the patient.

Wires, tubes, hoses and other conduits thus become suspended between the patient and the device or machine they are coupled to. Such wires etc. creates an inconvenient mass that only has a tendency to impede the work of caretakers, while also severely limiting the movement of the patient, since excessive movement may cause some vital monitoring equipment to become detached.

A commonly employed solution is to attach the wires, tubes, hoses etc. to the frame of the patient's bed, or some other support surface, with tape or some other crude means of attachment. This conveniently grants easier access for caretakers, such as doctors and nurses, to the patient. However, tying the tubes etc. down in such a fashion only further limits the movement of the patient, since the tension on the tubes etc. is only increased, which in turn decreases the amount of pull that is required for same to become detached.

Accordingly, a need remains for a breather hose supporting apparatus in order to overcome the above-noted shortcoming. The present invention satisfies such a need by providing a directional hose guide that is easy to install and use, durable in design, attachable to many surfaces, increases the patient's comfort and grants easier access for caretakers to the patient. The pivoting nature of such a directional hose guide allows a patient to easily move about without the danger of accidentally pulling a cord, hose or tube from its connection point. The attachment clamp also allows the hose guide to be suspended from any number of support surfaces, ranging from bed frames to tables, without interfering with the patient's care. Such a directional hose guide is especially appealing to hospitals, nursing homes, veterinary clinics, dental offices and walk-in-clinics, to name only a few.

BRIEF SUMMARY OF THE INVENTION

In view of the foregoing background, it is therefore an object of the present invention to provide a breather hose supporting apparatus. These and other objects, features, and advantages of the invention are provided by an adaptable hose guide for supporting breather hoses in a medical care environment.

The hose guide includes an elongated base plate that has a centrally disposed longitudinal axis and further has top and bottom surfaces. Such a top surface includes a fastening member extending along a longitudinal length thereof. The bottom surface includes a plurality of monolithically formed guides extending downward therefrom. One of the guides has a monolithically formed eyelet situated adjacent to an end portion of the base plate.

The bottom surface further has a monolithically formed protrusion extending downwardly therefrom. Such a protrusion has an aperture formed medially therein wherein the aperture traverses the axis. The aperture further has a lip portion extending inwardly along a perimeter thereof.

A hose support has a generally annular shape and further has a centrally formed aperture for advantageously and effectively receiving breather hoses therethrough. Such a hose support has a concave outer surface suitably sized and shaped for guiding a breather hose therealong. The hose support includes a plurality of monolithically formed finger members extending vertically away therefrom and is directly and rotatably connectable to the protrusion. Such a hose support is selectively articulatable along an arcuate path extending 360 degrees. The finger members engage the lip portion in such a manner that the hose support can conveniently be maintained at a stable position subjacent to the base plate. The hose support further includes a permanently connected inner layer. The present invention also includes a tether. Such a tether is formed from elastic material.

A stop member has a generally annular shape and a plurality of flange portions monolithically formed therewith. The flange portions diverge downwardly therefrom wherein one of the flange portions has an aperture formed therein. Such an aperture receives the tether therethrough such that the stop member can be adjustably attached to the eyelet. The stop member is spaced from the attaching mechanism. The stop member may be formed from flexible and non-corrosive material such that a plurality of hoses can advantageously and effectively be positioned therethrough and maintained at a static position to prevent tangling during operating conditions.

A mechanism is included for attaching the hose guide to an elevated support surface. The attaching mechanism preferably includes a C-clamp that has upper and lower portions and further has a side portion monolithically formed with the upper and lower portions. Such an upper portion has an aperture formed medially therein. The lower and side portions include a fastening member extending along an exterior length thereof such that the C-clamp can effectively be removably and adjustably attached directly to the fastener of the base plate.

The attaching mechanism also includes a ring and an actuating arm operably positioned through the aperture. Such an actuating arm includes proximal and distal portions. The proximal portion is provided with a bore for receiving the ring therethrough. The actuating arm further includes a deformably resilient spring member positioned thereabout and adaptable between equilibrium and compressed positions. The distal portion includes a monolithically formed disc extending radially and horizontally about a longitudinal axis of the actuating arm. Such a disc is selectively adaptable between raised and lowered positions when the spring member is adapted between compressed and equilibrium positions respectively.

In use, a user selectively grasps the ring and adapts the spring member between compressed and equilibrium positions such that an elevated support surface can effectively be positioned between the disc and the lower portion of the C-clamp so that the base plate can be maintained at a substantially stable position during operating conditions.

In an alternate embodiment, the attaching mechanism may include a suction cup directly conjoined subjacent to the base plate. Such a suction cup is removably positional adjacent to an elevated support surface during operating conditions.

In yet another embodiment, the attaching mechanism preferably includes a plurality of flexible straps removably insertable through the guides. Such straps have an adjustable length such that a user can advantageously adapt the straps about the elevated support surface. The inner layer of the straps preferably include hook and loop fastening material.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

FIG. 2 is side-elevational view of the attaching mechanism shown in FIG. 1;

FIG. 3 is a front-elevational view of the attaching mechanism shown in FIG. 2;

FIG. 4 is a top plan view of the attaching mechanism shown in FIG. 2;

FIG. 5 is a rear-elevational view of the attaching mechanism shown in FIG. 2;

FIG. 6 is a bottom plan view of the attaching mechanism shown in FIG. 2;

FIG. 14 is a side-elevational view of the stop member shown in FIG. 1;

FIG. 15 is a top plan view showing yet another embodiment of the attaching mechanism including the flexible straps, in accordance with the present invention;

FIG. 16 is a side-elevational view showing an alternate embodiment of the attaching mechanism including the suction cup, in accordance with the present invention; and FIG. 17 is a side-elevational view showing a final embodiment of the attaching mechanism including a threadably adaptable fastener and U-shaped clamp, in accordance with the present invention.

DETAILED DESCRIPTION OF THE INVENTION

Figure 1:
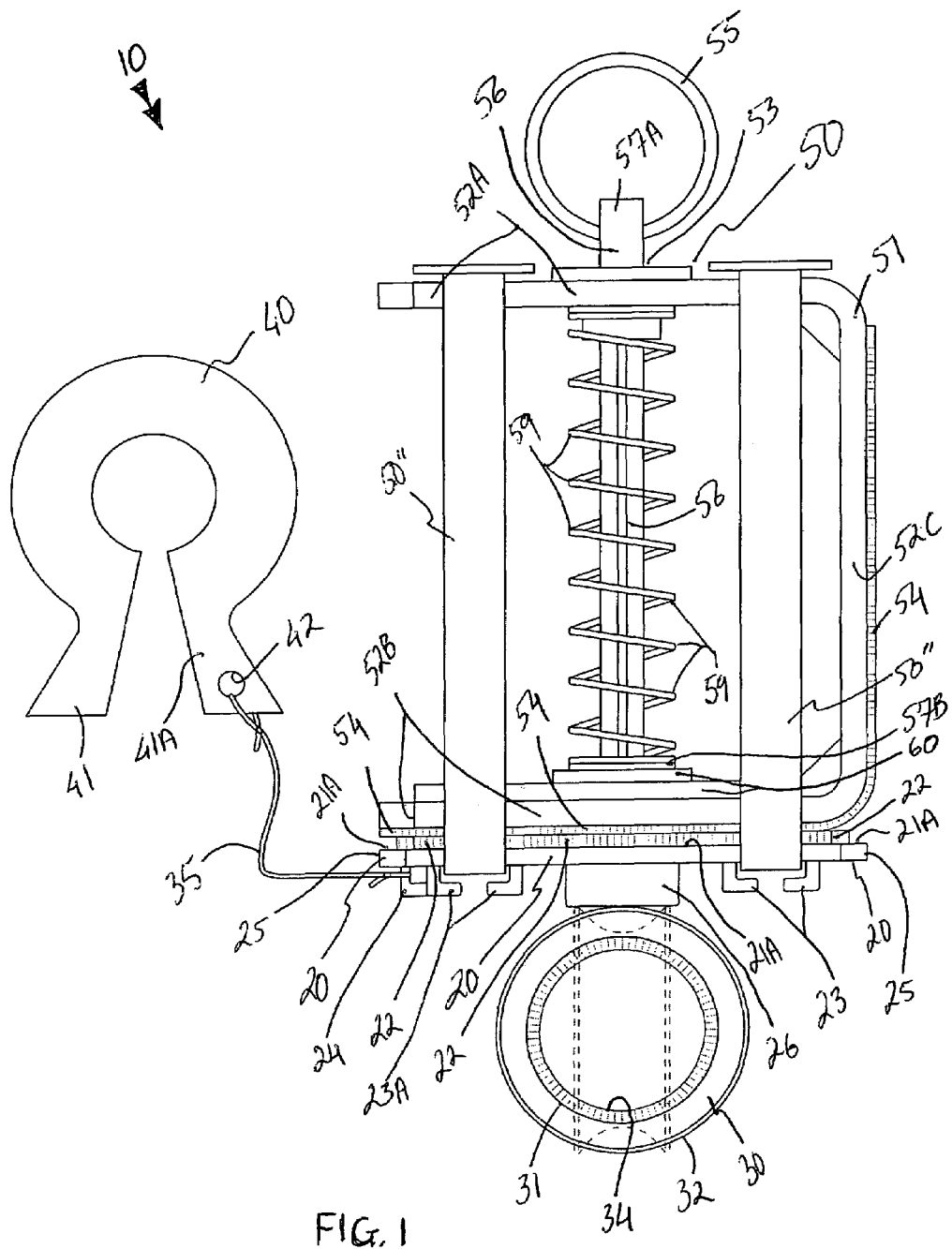
FIG. 1 is a side-elevational view showing a breather hose supporting apparatus, in accordance with the present invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this application will be thorough and complete, and will fully convey the true scope of the invention to those skilled in the art. Like numbers refer to like elements throughout the figures and prime, double prime and triple prime numbers refer to alternate embodiments of such elements.

The apparatus of this invention is referred to generally in FIGS. 1-17 by the reference numeral 10 and is intended to provide a breather hose supporting apparatus. It should be understood that the apparatus 10 may be used to support many different types of hoses and conduits and should not be limited in use to only breather hoses.

Referring initially to FIGS. 1 and 7 through 10, the apparatus 10 includes an elongated base plate 20 that has a centrally disposed longitudinal axis and further has top 21A and bottom 21B surfaces. Such a top surface 21A includes a fastening member 22 extending along a longitudinal length thereof. The fastening member 22 consists of the hook and loop fastener type and is preferably welded to top surface 21A such that fastening member 22 does not peel off during repeated and extended use. Of course, the fastening member 22 may consist of alternate fasteners, such as magnetic strips, as is obvious to a person of ordinary skill in the art so long as such alternate fasteners are securely conjoined directly to top surface 21A. The bottom surface 21B includes a plurality of monolithically formed guides 23 extending downward therefrom. One of the guides 23A has a monolithically formed eyelet 24 situated adjacent to an end portion 25A of the base plate 20. Of course, the base plate 20 may include an eyelet 24 formed at the other end portion 25B thereof as well, as is obvious to a person of ordinary skill in the art.

Figure 7:
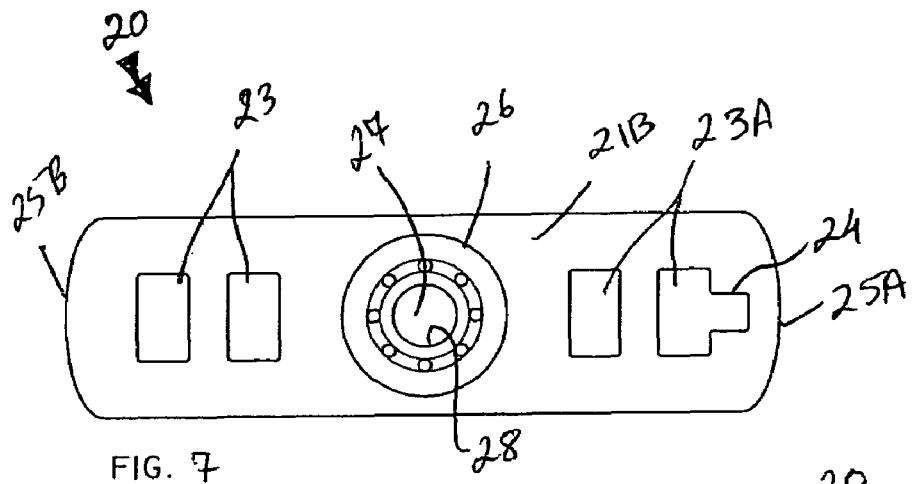
FIG. 7 is a top plan view of the base plate shown in FIG. 1.
Figure 8:
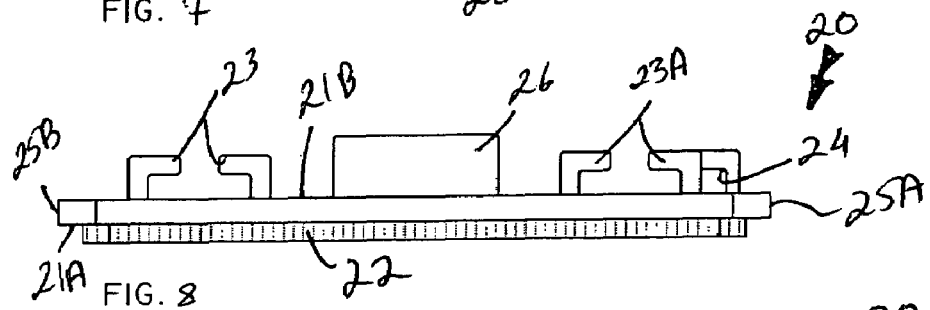
FIG. 8 is a side-elevational view of the base plate shown in FIG. 7.
Figure 9:
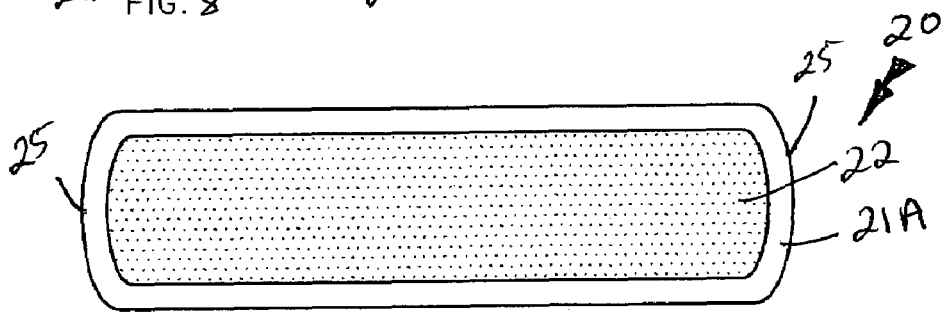
FIG. 9 is bottom plan view of the base plate shown in FIG. 8.
Figure 10:
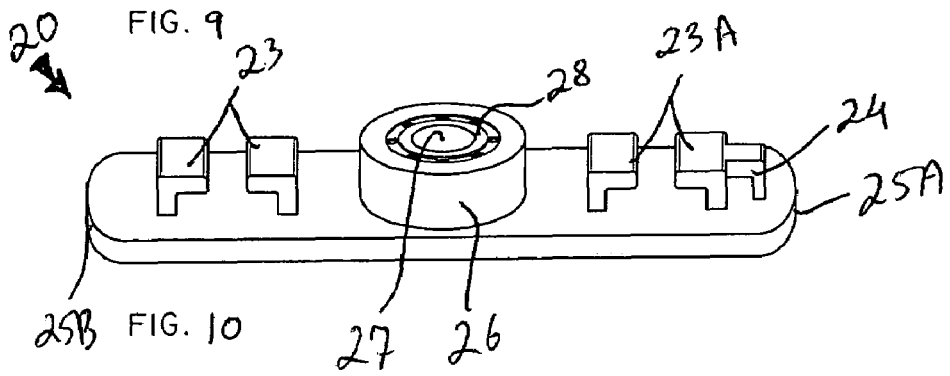
FIG. 10 is a perspective view of the base plate shown in FIG. 7.
Figure 11:
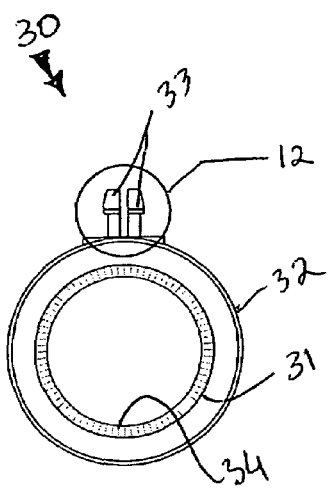
FIG. 11 is a side-elevational view of the hose support shown in FIG. 1.
Figure 13:
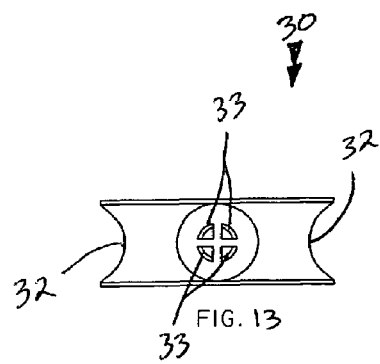
FIG. 13 is a top plan view of the hose support shown in FIG. 11.
Figure 12:
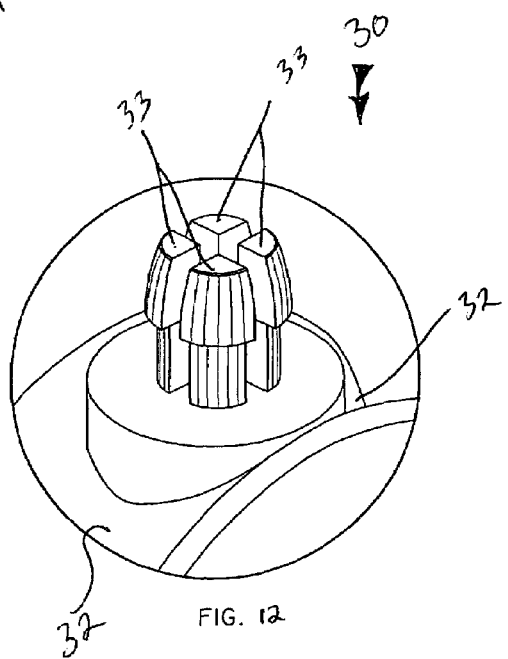
FIG. 12 is an enlarged perspective view of section 12 shown in FIG. 11, showing the finger members of the hose support.

Referring to FIGS. 1, 7, 8 and 10, the bottom surface 21B further has a monolithically formed protrusion 26 extending downwardly therefrom. Such a protrusion 26 has an aperture 27 formed medially therein wherein the aperture 27 traverses the axis. The aperture 27 further has a lip portion 28 extending inwardly along a perimeter thereof, as is best shown in FIGS. 7 and 10.

Referring to FIGS. 1, 11, 12, 13, 16 and 17, a hose support 30 has a generally annular shape and further has a centrally formed aperture 31 that is important for advantageously and effectively receiving breather hoses (not shown) therethrough. Of course, the hose support aperture 31 may be produced in a variety of alternate widths so as to effectively guide various amounts of hoses therethrough, as is obvious to a person of ordinary skill in the art. Such a hose support 30 has a concave outer surface 32 suitably sized and shaped for guiding a breather hose therealong.

The hose support 30 includes a plurality of monolithically formed finger members 33 extending vertically away therefrom that are directly and rotatably connectable, with no intervening elements, to the protrusion 26. Such a hose support 30 is selectively articulatable along an arcuate path extending 360 degrees. This is an essential feature for allowing a person attached to the breather hoses to have a greater range of movement without entangling or becoming entangled within the breather hoses. The finger members 33 are critical for effectively engaging the lip portion 28 in such a manner that the hose support 30 can conveniently be maintained at a stable position subjacent to the base plate 20. It is critical that finger members 33 are formed from hardened plastic or suitable polymers having high tensile strengths for reducing the likelihood of fatigue or creeping during extended use. Such finger members 33 should be constructed to have firm and stout shapes that can withstand repeated external forces during operating conditions. It is within the scope of this invention to manufacture such finger members 33 in alternate shapes having thicker and stronger operating characteristics as well known to a person of ordinary skill in the art.

The hose support 30 further includes a permanently affixed inner layer 34, preferably via welding procedures similar to fastening member 21A. Such an inner layer 34 is crucial for effectively preventing damage to hoses and other such conduits that are passing through the hose support 30. The present invention also includes a tether 35. Such a tether 35 is formed from elastic material. Of course, the tether 35 may be produced from alternate materials, such as rope or a link chain, as is obvious to a person of ordinary skill in the art.

Referring to FIGS. 1 and 14, a stop member 40 has a generally annular shape and a plurality of flange portions 41 monolithically formed therewith. The flange portions 41 diverge downwardly therefrom wherein one of the flange portions 41A has an aperture 42 formed therein. Such an aperture 42 receives the tether 35 therethrough such that the stop member 40 can be adjustably attached to the eyelet 24. This advantageously prevents the stop member 40 from becoming separated from the apparatus 10 and accidentally becoming misplaced. The stop member 40 is spaced from the attaching mechanism 30. Such a stop member 40 is formed from flexible and non-corrosive material such that a plurality of hoses can advantageously and effectively be positioned therethrough and maintained at a static position, which is critical for preventing tangling thereof during operating conditions.

Referring to FIGS. 1 through 6, a mechanism 50 is included for attaching the hose guide 30 to an elevated support surface. The attaching mechanism 50 includes a C-clamp 51 that has upper 52A and lower 52B portions and further has a side portion 52C monolithically formed with the upper 52A and lower 52B portions. Such an upper portion 52A has an aperture 53 formed medially therein. The lower 52B and side 52C portions include a fastening member 54 extending along an exterior length thereof such that the C-clamp 51 can effectively be removably and adjustably attached directly, with no intervening elements, to the fastener 22 of the base plate 20. Thus, the base plate 20 can either be attached to the lower portion 52B or the side portion 52C depending on the operating conditions. The C-clamp fastening member 54 consists of the hook and loop fastener type and is permanently welded to 52B and 52C in a similar manner described hereinabove. Of course, the fastening member 54 may consist of alternate fasteners, such as magnetic strips, as is obvious to a person of ordinary skill in the art.

Referring to FIGS. 1 through 5, the attaching mechanism 50 also includes a ring 55 and an actuating arm 56 operably positioned through the aperture 53. Such an actuating arm 56 includes proximal 57A and distal 57B portions. The proximal portion 57A is provided with a bore 58 for receiving the ring 55 therethrough. The actuating arm 56 further includes a deformably resilient spring member 59 positioned thereabout and adaptable between equilibrium and compressed positions. The distal portion 57B includes a monolithically formed disc 60 extending radially and horizontally about a longitudinal axis of the actuating arm 56. Such a disc 60 is selectively adaptable between raised and lowered positions when the spring member 59 is adapted between compressed and equilibrium positions respectively. The disc 60 and spring member 59 are vital and advantageous for ensuring that the C-clamp 51 remains fixedly attached to the support surface while the hose support 30 rotates freely from the base plate 20 attached thereto.

In use, a user selectively grasps the ring 55 and adapts the spring member 59 between compressed and equilibrium positions such that an elevated support surface can effectively be positioned between the disc 60 and the lower portion 52B of the C-clamp 51 so that the base plate 20 can advantageously and effectively be maintained at a substantially stable position during operating conditions.

Referring to FIG. 16, in an alternate embodiment 10', the attaching mechanism 50' includes a suction cup 61 directly conjoined, with no intervening elements, subjacent to the hose support 30'. Such a suction cup 61 is removably positional adjacent to an elevated support surface during operating conditions. The suction cup 61 can advantageously and conveniently be attached to smooth surfaces, such as a wall or mirror, where the C-clamp 51 of the attachment mechanism 50 can not.

Referring to FIGS. 1 and 15, in yet another embodiment 10", the attaching mechanism 50" includes a plurality of flexible straps 62 removably insertable through the guides 23. Such straps 62 have an adjustable length, which is essential such that a user can advantageously adapt the straps 62 about the elevated support surface. The inner layer (not shown) of the straps 62 include hook and loop fastening material. A preferred operational embodiment of the apparatus 10 is shown in FIG. 1, where the attaching mechanisms 50 and 50" are employed simultaneously in order to provide the greatest amount of stabilization to the apparatus 10.

Referring to FIG. 17, in a final embodiment 10''', the attaching mechanism 50 includes a U-shaped clamp member 63. Such a U-shaped clamp member 63 has monolithically formed top 64A, bottom 64B and side 64C portions. The top portion 64A has a hose support 30''' rotatably attached thereto. The bottom portion 64B includes a fastening member 65, with axially opposed end portions 66, threadably engaged therewith. One such an end portion 66A has a conical disc 67 attached thereto that is essential for maintaining the apparatus 10''' at a stable position when the fastening member 65 is adapted to a closed position. Another end portion 66B includes a substantially annular flattened region 67 directly attached thereto, with no intervening elements, for providing convenient gripping area about which a user may grasp and rotate the fastening member 65.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. An adaptable hose guide for supporting breather hoses in a medical care environment, said hose guide comprising:
    a elongated base plate having a centrally disposed longitudinal axis and further having top and bottom surfaces, said top surface including a fastening member extending along a longitudinal length thereof, said bottom surface including a plurality of monolithically formed guides extending downward therefrom, one said guides having a monolithically formed eyelet situated adjacent an end portion of said base plate, said bottom surface further having a monolithically formed protrusion extending downwardly therefrom, said protrusion having an aperture formed medially therein wherein the aperture traverses the axis, the aperture further having a lip portion extending inwardly along a perimeter thereof;
    a hose support having a generally annular shape and further having a centrally formed aperture for receiving breather hoses therethrough, said hose support including a plurality of monolithically formed finger members extending vertically away therefrom and being directly and rotatably connectable to said protrusion, said hose support being selectively articulatable along an arcuate path extending 360 degrees, said finger members engaging said lip portion in such a manner that said hose support can be maintained at a stable position subjacent said base plate, said hose support further including a permanently connected inner layer;
    a tether;
    a stop member having a generally annular shape and a plurality of flange portions monolithically formed therewith, said flange portions diverging downwardly therefrom wherein one said flange portions has an aperture formed therein, the aperture receiving said tether therethrough such that said stop member can be adjustably attached to said eyelet, said tether being formed from elastic material; and
    means for attaching said hose guide to an elevated support surface.

2. The hose guide of claim 1, wherein said attaching means comprises:
    a C-clamp having upper and lower portions and further having a side portion monolithically formed with said upper and lower portions, said upper portion having an aperture formed medially therein, said lower and side portions including a fastening member extending along an exterior length thereof such that said C-clamp can be removably and adjustably attached directly to said fastener of said base plate;
    a ring; and
    an actuating arm operably positioned through the aperture, said actuating arm including proximal and distal portions, said proximal portion being provided with a bore receiving said ring therethrough, said actuating arm further including a deformably resilient spring member positioned thereabout and adaptable between equilibrium and compressed positions, said distal portion including a monolithically formed disc extending radially and horizontally about a longitudinal axis of said actuating arm, said disc being selectively adaptable between raised and lowered positions when said spring member is adapted between compressed and equilibrium positions respectively;
    wherein a user selectively grasps said ring and adapts said spring member between compressed and equilibrium positions such that an elevated support surface can be positioned between said disc and said lower portion of said C-clamp so that said base plate can be maintained at a substantially stable position during operating conditions.

3. The hose guide of claim 1, wherein said attaching means comprises: a suction cup directly conjoined subjacent said base plate, said suction cup being removably positional adjacent to an elevated support surface during operating conditions.

4. The hose guide of claim 1, wherein said attaching means comprises: a plurality of flexible straps removably insertable through said guides, said straps having an adjustable length such that a user can adapt said straps about the elevated support surface.

5. The hose guide of claim 4, wherein said inner layer and said straps comprise: hook and loop fastening material.

6. The hose guide of claim 1, wherein said stop member is formed from flexible and non-corrosive material such that a plurality of hoses can be positioned therethrough and maintained at a static position to prevent tangling during operating conditions.

7. An adaptable hose guide for supporting breather hoses in a medical care environment, said hose guide comprising:
    a elongated base plate having a centrally disposed longitudinal axis and further having top and bottom surfaces, said top surface including a fastening member extending along a longitudinal length thereof, said bottom surface including a plurality of monolithically formed guides extending downward therefrom, one said guides having a monolithically formed eyelet situated adjacent an end portion of said base plate, said bottom surface further having a monolithically formed protrusion extending downwardly therefrom, said protrusion having an aperture formed medially therein wherein the aperture traverses the axis, the aperture further having a lip portion extending inwardly along a perimeter thereof;
    a hose support having a generally annular shape and further having a centrally formed aperture for receiving breather hoses therethrough, said hose support having a concave outer surface suitably sized and shaped for guiding a breather hose therealong, said hose support including a plurality of monolithically formed finger members extending vertically away therefrom and being directly and rotatably connectable to said protrusion, said hose support being selectively articulatable along an arcuate path extending 360 degrees, said finger members engaging said lip portion in such a manner that said hose support can be maintained at a stable position subjacent said base plate, said hose support further including a permanently connected inner layer;

a tether;

a stop member having a generally annular shape and a plurality of flange portions monolithically formed therewith, said flange portions diverging downwardly therefrom wherein one said flange portions has an aperture formed therein, the aperture receiving said tether therethrough such that said stop member can be adjustably attached to said eyelet, said tether being formed from elastic material; and means for attaching said hose guide to an elevated support surface.

8. The hose guide of claim 7, wherein said attaching means comprises:

a C-clamp having upper and lower portions and further having a side portion monolithically formed with said upper and lower portions, said upper portion having an aperture formed medially therein, said lower and side portions including a fastening member extending along an exterior length thereof such that said C-clamp can be removably and adjustably attached directly to said fastener of said base plate;

a ring; and an actuating arm operably positioned through the aperture, said actuating arm including proximal and distal portions, said proximal portion being provided with a bore receiving said ring therethrough, said actuating arm further including a deformably resilient spring member positioned thereabout and adaptable between equilibrium and compressed positions, said distal portion including a monolithically formed disc extending radially and horizontally about a longitudinal axis of said actuating arm, said disc being selectively adaptable between raised and lowered positions when said spring member is adapted between compressed and equilibrium positions respectively;

wherein a user selectively grasps said ring and adapts said spring member between compressed and equilibrium positions such that an elevated support surface can be positioned between said disc and said lower portion of said C-clamp so that said base plate can be maintained at a substantially stable position during operating conditions.

9. The hose guide of claim 7, wherein said attaching means comprises: a suction cup directly conjoined subjacent said base plate, said suction cup being removably positional adjacent to an elevated support surface during operating conditions.

10. The hose guide of claim 7, wherein said attaching means comprises: a plurality of flexible straps removably insertable through said guides, said straps having an adjustable length such that a user can adapt said straps about the elevated support surface.

11. The hose guide of claim 10, wherein said inner layer and said straps comprise: hook and loop fastening material.

12. The hose guide of claim 7, wherein said stop member is formed from flexible and non-corrosive material such that a plurality of hoses can be positioned therethrough and maintained at a static position to prevent tangling during operating conditions.

13. An adaptable hose guide for supporting breather hoses in a medical care environment, said hose guide comprising:

a elongated base plate having a centrally disposed longitudinal axis and further having top and bottom surfaces, said top surface including a fastening member extending along a longitudinal length thereof, said bottom surface including a plurality of monolithically formed guides extending downward therefrom, one said guides having a monolithically formed eyelet situated adjacent an end portion of said base plate, said bottom surface further having a monolithically formed protrusion extending downwardly therefrom, said protrusion having an aperture formed medially therein wherein the aperture traverses the axis, the aperture further having a lip portion extending inwardly along a perimeter thereof;

a hose support having a generally annular shape and further having a centrally formed aperture for receiving breather hoses therethrough, said hose support having a concave outer surface suitably sized and shaped for guiding a breather hose therealong, said hose support including a plurality of monolithically formed finger members extending vertically away therefrom and being directly and rotatably connectable to said protrusion, said hose support being selectively articulatable along an arcuate path extending 360 degrees, said finger members engaging said lip portion in such a manner that said hose support can be maintained at a stable position subjacent said base plate, said hose support further including a permanently connected inner layer;

a tether;

a stop member having a generally annular shape and a plurality of flange portions monolithically formed therewith, said flange portions diverging downwardly therefrom wherein one said flange portions has an aperture formed therein, the aperture receiving said tether therethrough such that said stop member can be adjustably attached to said eyelet, said tether being formed from elastic material, said stop member being spaced from said attaching means; and means for attaching said hose guide to an elevated support surface.

14. The hose guide of claim 13, wherein said attaching means comprises:

a C-clamp having upper and lower portions and further having a side portion monolithically formed with said upper and lower portions, said upper portion having an aperture formed medially therein, said lower and side portions including a fastening member extending along an exterior length thereof such that said C-clamp can be removably and adjustably attached directly to said fastener of said base plate;

a ring; and an actuating arm operably positioned through the aperture, said actuating arm including proximal and distal portions, said proximal portion being provided with a bore receiving said ring therethrough, said actuating arm further including a deformably resilient spring member positioned thereabout and adaptable between equilibrium and compressed positions, said distal portion including a monolithically formed disc extending radially and horizontally about a longitudinal axis of said actuating arm, said disc being selectively adaptable between raised and lowered positions when said spring member is adapted between compressed and equilibrium positions respectively;

wherein a user selectively grasps said ring and adapts said spring member between compressed and equilibrium positions such that an elevated support surface can be positioned between said disc and said lower portion of said C-clamp so that said base plate can be maintained at a substantially stable position during operating conditions.

15. The hose guide of claim 13, wherein said attaching means comprises: a suction cup directly conjoined subjacent said base plate, said suction cup being removably positional adjacent to an elevated support surface during operating conditions.

16. The hose guide of claim 13, wherein said attaching means comprises: a plurality of flexible straps removably insertable through said guides, said straps having an adjustable length such that a user can adapt said straps about the elevated support surface.

17. The hose guide of claim 16, wherein said inner layer and said straps comprise: hook and loop fastening material.

18. The hose guide of claim 13, wherein said stop member is formed from flexible and non-corrosive material such that a plurality of hoses can be positioned therethrough and maintained at a static position to prevent tangling during operating conditions.

* * * * *